(12) United States Patent
Tischler

(10) Patent No.: US 7,381,217 B2
(45) Date of Patent: Jun. 3, 2008

(54) SERPENTINE STENT PATTERN

(75) Inventor: Brian Tischler, New Brighton, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 230 days.

(21) Appl. No.: 11/317,604

(22) Filed: Dec. 23, 2005

(65) Prior Publication Data

US 2007/0150048 A1    Jun. 28, 2007

(51) Int. Cl.
 *A61F 2/06* (2006.01)
(52) U.S. Cl. ..................... 623/1.16; 623/1.22
(58) Field of Classification Search ............... 623/1.15, 623/1.16, 1.22, 1.23; *A61F 2/06*
See application file for complete search history.

(56) References Cited

U.S. PATENT DOCUMENTS

| | | | |
|---|---|---|---|
| 5,776,161 A | 7/1998 | Globerman | 606/194 |
| 5,876,449 A | 3/1999 | Starck et al. | 623/12 |
| 5,911,754 A | 6/1999 | Kanesaka et al. | 623/1.15 |
| 5,922,021 A | 7/1999 | Jang | 623/1 |
| 6,113,627 A | 9/2000 | Jang | 623/1 |
| 6,123,721 A | 9/2000 | Jang | 623/1 |
| 6,193,747 B1 | 2/2001 | Von Oepen | 623/1.15 |
| 6,200,334 B1 | 3/2001 | Jang | 623/1.1 |
| 6,331,189 B1 | 12/2001 | Wolinsky et al. | 623/1.15 |
| 6,348,065 B1 | 2/2002 | Brown et al. | 623/1.16 |
| 6,409,761 B1 | 6/2002 | Jang | 623/6.12 |
| 6,464,722 B2 | 10/2002 | Israel et al. | 623/1.17 |
| 6,468,302 B2 | 10/2002 | Cox et al. | 623/1.15 |
| 6,602,285 B1 | 8/2003 | Von Oepen et al. | 623/1.17 |
| 6,730,116 B1 | 5/2004 | Wolinsky et al. | 623/1.16 |
| 6,770,088 B1 | 8/2004 | Jang | 623/1.16 |
| 6,997,944 B2 * | 2/2006 | Harrison et al. | 623/1.15 |
| 7,223,283 B2 * | 5/2007 | Chouinard | 623/1.15 |
| 2001/0056298 A1 | 12/2001 | Brown et al. | 623/1.16 |
| 2002/0007212 A1 | 1/2002 | Brown et al. | 623/1.16 |
| 2002/0040236 A1 | 4/2002 | Lau et al. | 623/1.12 |
| 2002/0095208 A1 | 7/2002 | Gregorich et al. | 623/1.15 |
| 2002/0111669 A1 | 8/2002 | Pazienza et al. | 623/1.15 |
| 2002/0156525 A1 * | 10/2002 | Smith et al. | 623/1.22 |
| 2004/0073290 A1 * | 4/2004 | Chouinard | 623/1.15 |
| 2004/0267353 A1 | 12/2004 | Gregorich | 623/1.16 |
| 2005/0015136 A1 | 1/2005 | Ikeuchi et al. | 623/1.15 |
| 2005/0149168 A1 | 7/2005 | Gregorich | 623/1.15 |
| 2007/0150046 A1 * | 6/2007 | Meyer et al. | 623/1.15 |

FOREIGN PATENT DOCUMENTS

| | | |
|---|---|---|
| DE | 19840645 | 3/2000 |
| EP | 0 884 029 A1 | 12/1998 |
| WO | WO 99/38457 | 8/1999 |
| WO | WO 01/01885 A1 | 1/2001 |
| WO | WO 01/01889 | 1/2001 |
| WO | WO 01/41675 | 6/2001 |
| WO | WO 2004/045474 | 6/2004 |

* cited by examiner

*Primary Examiner*—Brian Pellegrino
*Assistant Examiner*—Jason-Dennis Stewart
(74) *Attorney, Agent, or Firm*—Vidas, Arrett & Steinkraus, P.A.

(57) ABSTRACT

A stent comprises a serpentine band. The serpentine band has alternating peaks and troughs. A first set of peaks and troughs define an envelope of generally increasing longitudinal extent in a distal direction and a second set of peaks and troughs define an envelope of generally increasing longitudinal extent in a proximal direction.

10 Claims, 10 Drawing Sheets

SERPENTINE STENT PATTERN

FIELD OF THE INVENTION

In some embodiments this invention relates to implantable medical devices, their manufacture, and methods of use. Some embodiments are directed to delivery systems, such as catheter systems of all types, which are utilized in the delivery of such devices.

DESCRIPTION OF THE RELATED ART

A stent is a medical device introduced to a body lumen and is well known in the art. Typically, a stent is implanted in a blood vessel at the site of a stenosis or aneurysm endoluminally, i.e. by so-called "minimally invasive techniques" in which the stent in a radially reduced configuration, optionally restrained in a radially compressed configuration by a sheath and/or catheter, is delivered by a stent delivery system or "introducer" to the site where it is required. The introducer may enter the body from an access location outside the body, such as through the patient's skin, or by a "cut down" technique in which the entry blood vessel is exposed by minor surgical means.

Stents, grafts, stent-grafts, vena cava filters, expandable frameworks, and similar implantable medical devices, collectively referred to hereinafter as stents, are radially expandable endoprostheses which are typically intravascular implants capable of being implanted transluminally and enlarged radially after being introduced percutaneously.

Stents may be self-expanding, expanded by an internal radial force, such as when mounted on a balloon, or a combination of self-expanding and balloon expandable (hybrid expandable).

Stents may be created by methods including cutting or etching a design from a tubular stock, from a flat sheet which is cut or etched and which is subsequently rolled or from one or more interwoven wires or braids.

Stents may be implanted in a variety of body lumens or vessels such as within the vascular system, urinary tracts, bile ducts, fallopian tubes, coronary vessels, secondary vessels, etc. Stents may be used to reinforce body vessels and to prevent restenosis following angioplasty in the vascular system.

It is in particular desirable to have a stent which may be used in the superficial femoral artery (SFA) or in other vessels where high axial and bending compliance is required. SFA vessels are known for their high degree of elasticity and motion including axial compression/stretch, bend, kink, twist and flattening. It is desired that a stent implant have similar properties mechanically to the vessel in which it is implanted while still maintaining sufficient radial force to keep the vessel propped open. Fractures have been observed in the femoral-popliteal artery beds for a number of commercial Nitinol self-expanding stents which rely on a stiff metallic connector to connect adjacent radial serpentine segments. Axial or bending force is transmitted through these connectors to the serpentine rings since the connectors cannot significantly bend to accommodate the change in stent shape.

Typically, designing the stent's serpentine rings to be more flexible creates more axial or bending compliant stents, but results in a tradeoff in radial expansion force. De-coupling radial force with axial compliance would be desirable.

The art referred to and/or described above is not intended to constitute an admission that any patent, publication or other information referred to herein is "prior art" with respect to this invention. In addition, this section should not be construed to mean that a search has been made or that no other pertinent information as defined in 37 C.F.R. §1.56(a) exists.

All US patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well only for the purposes of complying with 37 C.F.R. 1.72. The abstract is not intended to be used for interpreting the scope of the claims.

BRIEF SUMMARY OF THE INVENTION

This invention contemplates a number of embodiments where any one, any combination of some, or all of the embodiments can be incorporated into a stent and/or a stent delivery system and/or a method of use.

In one embodiment, the invention is directed to a stent comprising a serpentine band disposed about the longitudinal axis. The serpentine band has a plurality of proximal turns and distal turns. Each strut extends between one proximal turn and one distal turn. The distal turns are arranged in a pattern of increasing and decreasing extent in a proximal direction. The pattern includes at least one set of three or more consecutive interconnected peaks and troughs of decreasing proximal extent followed by at least one set of three or more consecutive interconnected peaks and troughs of increasing proximal extent.

In some embodiment, the stent will comprise a plurality of the serpentine band, adjacent serpentine bands connected one to the other.

In some embodiments of the invention, the pattern of increasing and decreasing extent may consist of only one set of at least three consecutive interconnected peaks and troughs of decreasing proximal extent followed by only one set at least three consecutive interconnected peaks and troughs of increasing proximal extent. In other embodiments of the invention, the pattern of increasing and decreasing extent comprises at least two sets of three of three or more consecutive interconnected peaks and troughs of decreasing proximal extent followed by at least two sets of three or more consecutive interconnected peaks and troughs of increasing proximal extent.

In some embodiments of the invention, the serpentine bands are substantially in phase with one another.

In some embodiments of the invention, the serpentine band is at the proximal end of the stent, the stent including a helical portion extending from the serpentine band.

In some embodiments of the invention, the stent comprises two of the serpentine bands. One of the serpentine bands is located at a proximal end of the stent and the other of the serpentine bands is located at the distal end of the stent. The stent includes a helical band extending between the two serpentine bands.

In some embodiments, the invention is directed to a stent comprising a serpentine band, the serpentine band having alternating peaks and troughs, a first set of peaks and troughs defining an envelope of generally increasing longitudinal extent in a distal direction and a second set of peaks and troughs defining an envelope of generally increasing longitudinal extent in a proximal direction.

Optionally, the first set of peaks and troughs and the second set of peaks and troughs may form a closed ring which extends about the longitudinal axis of the stent.

Optionally, the serpentine band or bands may each further comprises a third set of peaks and trough and a fourth set of peaks and troughs. The third set of peaks and troughs define an envelope of generally increasing longitudinal extent in a distal direction and the fourth set of peaks and troughs define an envelope of generally increasing longitudinal extent in a proximal direction.

In some embodiments, every other peak and every other trough of the first set of peaks and troughs is of increasing longitudinal extent in a distal direction and every other peak and every other trough of the second set of peaks and troughs is of increasing longitudinal extent in a proximal direction.

In other embodiments, every peak and every trough of the first set of peaks and troughs is of increasing longitudinal extent in a distal direction and every peak and every trough of the second set of peaks and troughs is of increasing longitudinal extent in a proximal direction.

The invention is also directed to a stent have a serpentine band, the serpentine band having alternating peaks and troughs, the peaks and troughs disposed about an imaginary midline which extends midway between the peaks and the troughs, where the imaginary midline includes a portion with a positive slope and a portion with a negative slope.

In some embodiments of the invention, the stent may comprise a plurality of the serpentine band, adjacent serpentine bands connected one to the other.

In some embodiments of the invention, the serpentine band includes a first portion having a positive slope and a third portion having a positive slope and a second portion having a negative slope, and a fourth portion having a negative slope. The second portion disposed between the first and third portions and the third portion disposed between the second and fourth portions.

These and other embodiments which characterize the invention are pointed out with particularity in the claims annexed hereto and forming a part hereof. However, for additional understanding of the invention, its advantages and objectives obtained by its use, reference should be made to the drawings which form a further part hereof and the accompanying descriptive matter, in which there is illustrated and described embodiments of the invention.

BRIEF DESCRIPTION OF THE SEVERAL VIEWS OF THE DRAWING(S)

A detailed description of the invention is hereafter described with specific reference being made to the drawings.

DETAILED DESCRIPTION OF THE INVENTION

Figure 1:
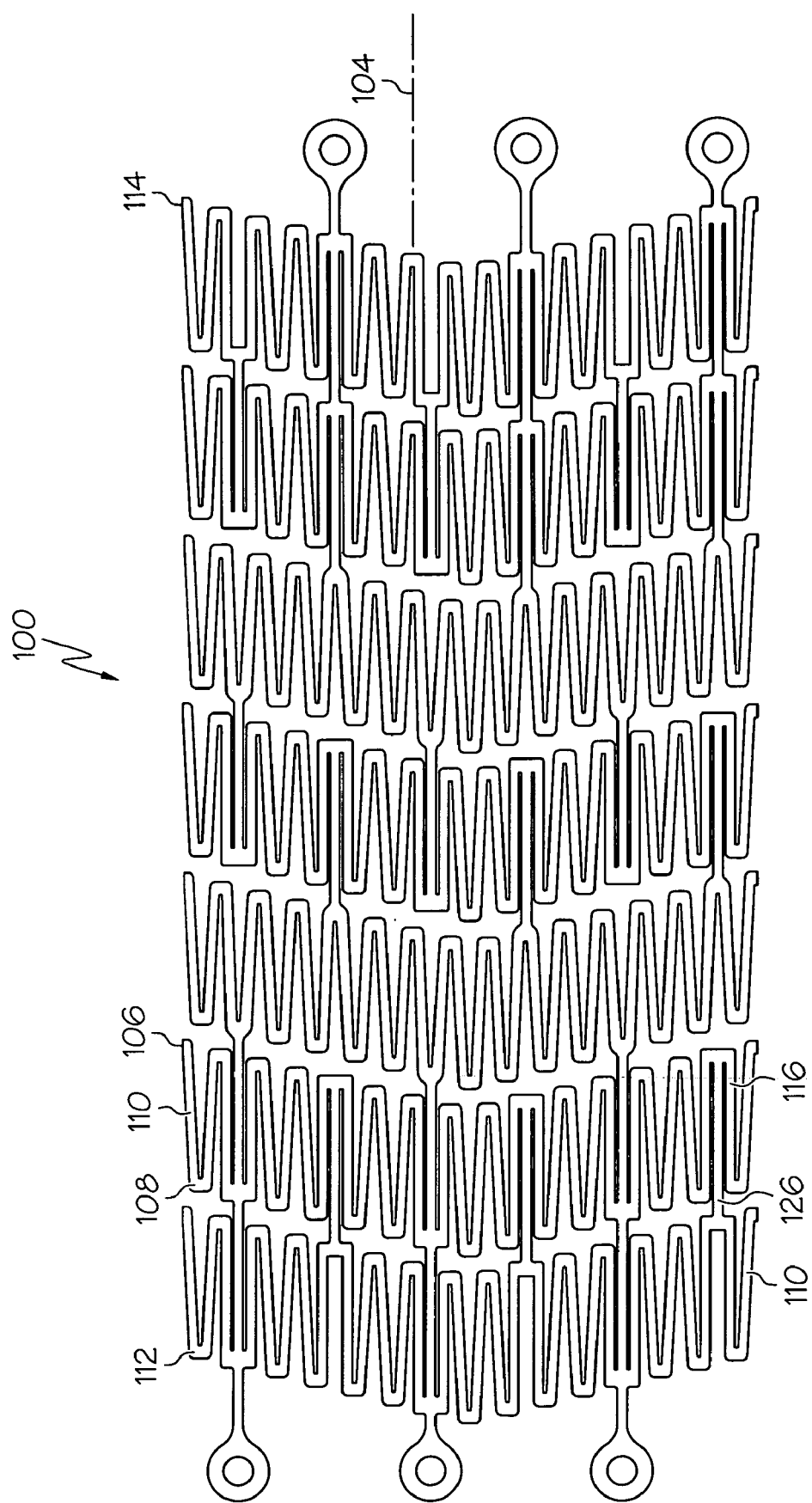
FIG. 1 shows a flat pattern of an inventive stent.

While this invention may be embodied in many different forms, there are described in detail herein specific embodiments of the invention. This description is an exemplification of the principles of the invention and is not intended to limit the invention to the particular embodiments illustrated.

For the purposes of this disclosure, like reference numerals in the figures shall refer to like features unless otherwise indicated.

Figure 2:
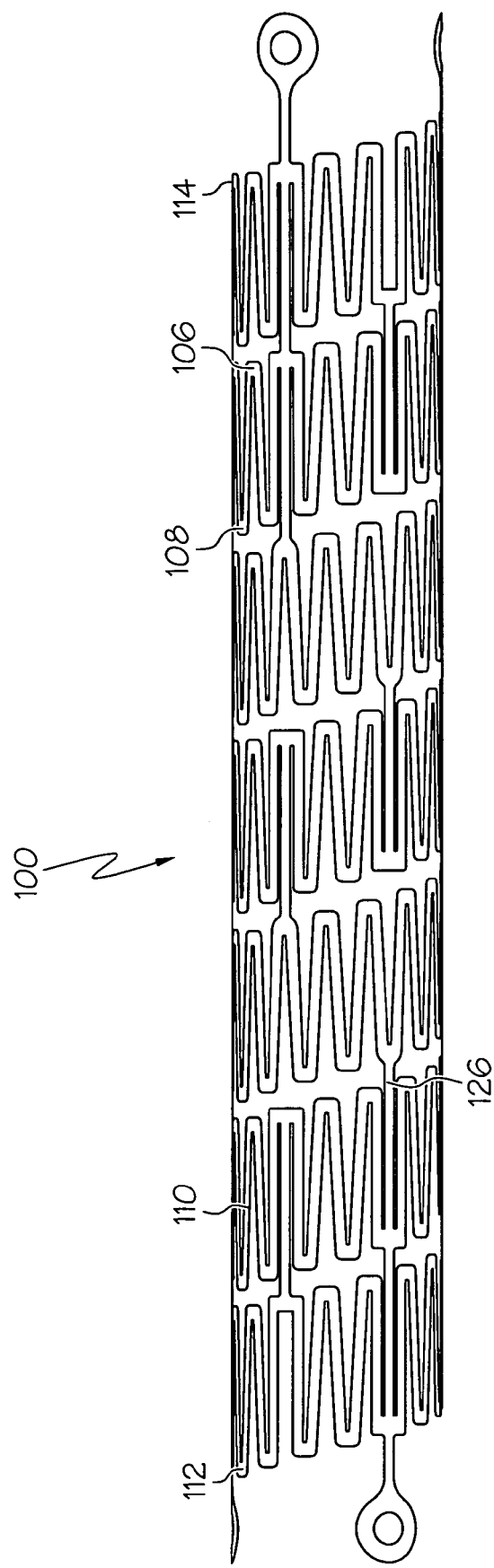
FIG. 2 shows the stent corresponding to the flat pattern of FIG. 1.

In one embodiment, the invention is directed to a stent as shown by way of example in FIGS. 1 and 2. FIG. 1 shows a flat pattern of an inventive stent and FIG. 2 shows the stent in its cylindrical form. Stent 100 comprising a serpentine band 110 disposed about the longitudinal axis 104 of the stent. Serpentine band 110 has a plurality of proximal turns 106 and distal turns 108. Each strut 116 extends between one proximal turn 106 and one distal turn 108. Distal turns 108 are arranged in a pattern of increasing and decreasing extent in a proximal direction. The pattern includes at least one set of three or more consecutive interconnected peaks and troughs of decreasing proximal extent followed by at least one set of three or more consecutive interconnected peaks and troughs of increasing proximal extent. As shown in FIG. 1, the pattern includes fifteen struts which are joined at eight peaks of decreasing proximal extent and fifteen struts which are joined at eight peaks of increasing proximal extent.

Although it is within the scope of the invention for an inventive stent to have only a single such serpentine band, as shown in FIG. 1, the invention is also directed to stents having a plurality of such serpentine bands. The stent may have from two to twenty or more of such bands between the proximal end 112 and distal end 114 of the stent.

As such, in FIG. 1, adjacent serpentine bands 110 are interconnected by connectors 126. Connectors 126 in FIG. 1 are straight. It is within the scope of the invention for the connectors to be straight or to have one or more curved sections. The connectors, for example, may be C-shaped, S-shaped or may be of a different curved shape. The connectors, whether straight or having one or more curved sections, may have first and second ends which are longitudinally offset and circumferentially aligned as shown in FIG. 1, or may have first and second ends which are longitudinally offset and circumferentially offset. The latter connectors would include connectors which are not parallel to the longitudinal axis of the stent.

In some embodiments of the invention, such as that shown by way of example in FIG. 1, the pattern of increasing and decreasing extent may consist of only one set of at least three consecutive interconnected peaks and troughs of decreasing proximal extent followed by only one set at least three consecutive interconnected peaks and troughs of increasing proximal extent.

Figure 3:
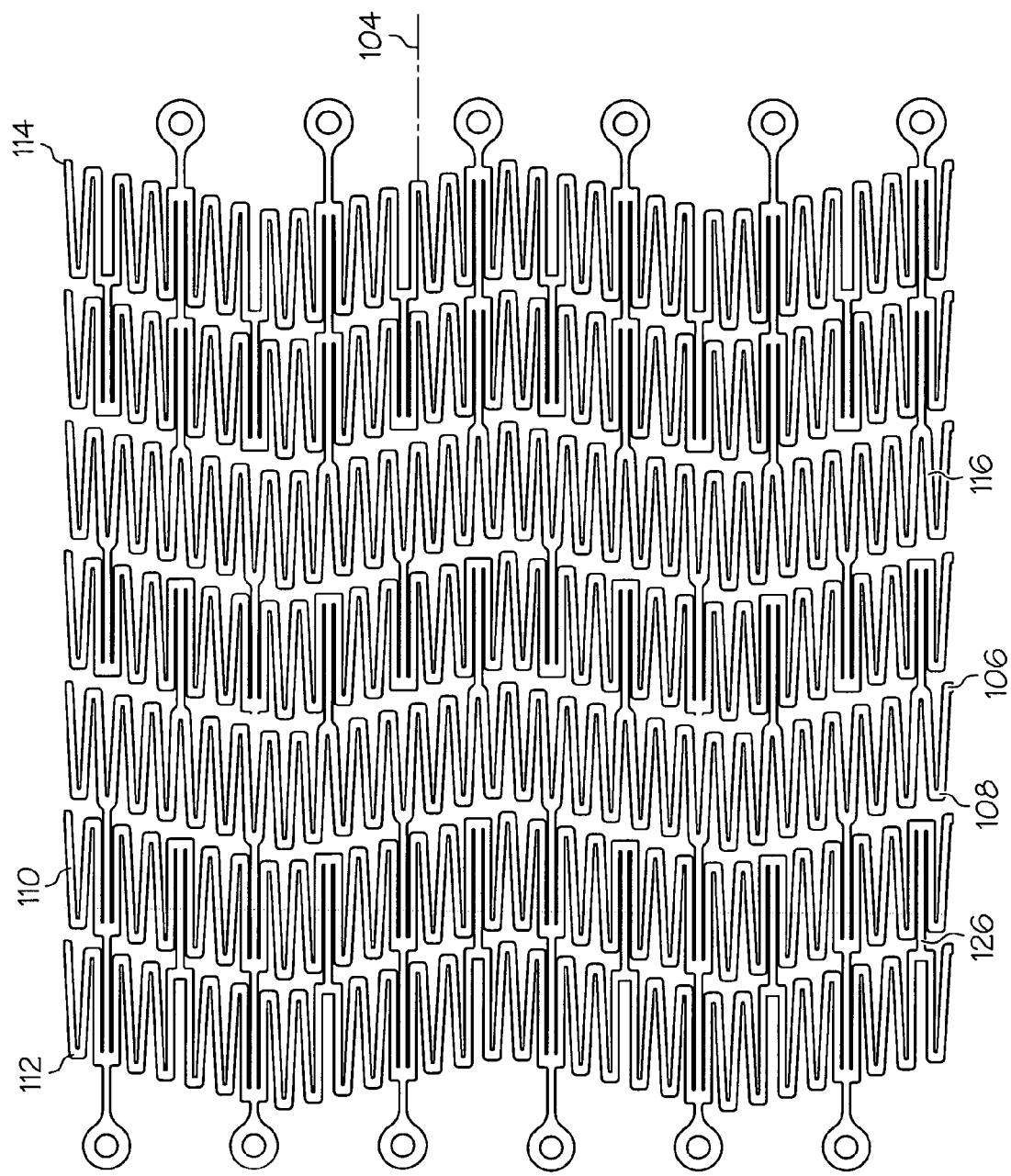
FIG. 3 shows a flat pattern of another inventive stent with two positive sloped and two negative sloped sections to make up the serpentine rings.

In other embodiments of the invention, as shown by way of example in FIG. 3, the pattern of increasing and decreasing extent comprises at least two sets of three of three or more consecutive interconnected peaks and troughs of decreasing proximal extent followed by at least two sets of three or more consecutive interconnected peaks and troughs of increasing proximal extent. The stent of FIG. 3 includes two such sets per serpentine band. It is within the scope of the invention to have three, four or more of such sets.

As shown in FIG. 3, each of the serpentine bands has a serpentine pattern of peaks and troughs. The pattern of peaks and troughs of decreasing and increasing proximal extent also defines a wavelength associated with the serpentine band.

Desirably, where the stent has more than one of the serpentine band, the serpentine bands are substantially in phase with one another. The term "substantially in phase include" encompasses adjacent serpentine bands which are up to 10 degrees out of phase with one another. Desirably, adjacent bands will be no more than 5 degrees out of phase with one another. More desirably, adjacent bands will be no more than 1 degree out of phase with one another.

In some embodiments, as shown by way of example in FIG. 1, the invention is directed to a stent comprising a serpentine band, the serpentine band having alternating peaks and troughs, a first set of peaks and troughs defining an envelope of generally increasing longitudinal extent in a distal direction and a second set of peaks and troughs defining an envelope of generally increasing longitudinal extent in a proximal direction.

Optionally, as shown in FIG. 1, the first set of peaks and troughs and the second set of peaks and troughs may form a closed ring which extends about the longitudinal axis of the stent.

Optionally, as shown in embodiment of FIG. 3, the serpentine band or bands may each further comprises a third set of peaks and trough and a fourth set of peaks and troughs. The third set of peaks and troughs define an envelope of generally increasing longitudinal extent in a distal direction and the fourth set of peaks and troughs define an envelope of generally increasing longitudinal extent in a proximal direction.

Figure 4:
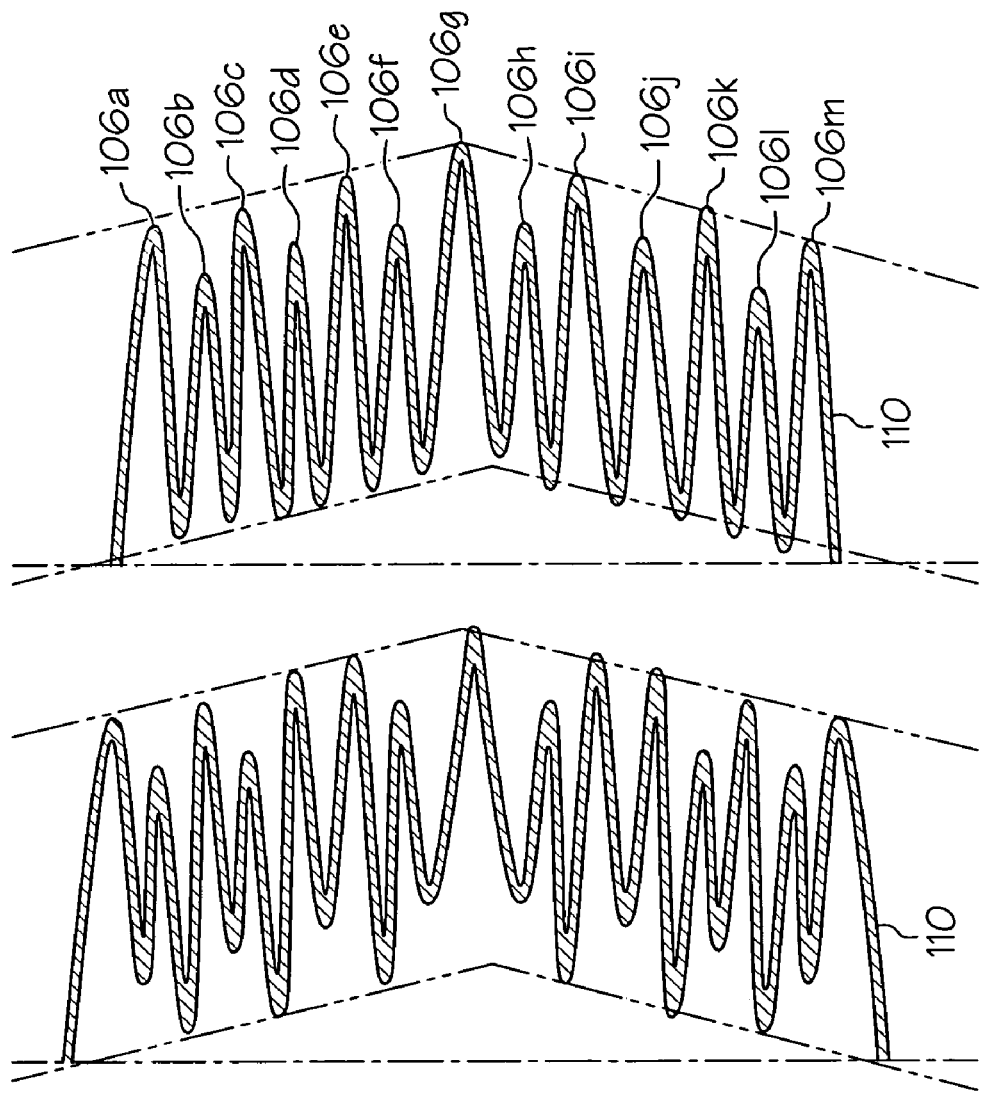
FIG. 4 shows serpentine rings for use in inventive stents where every other peak and every other trough of the first set of peaks and troughs is of increasing longitudinal extent in a distal direction and every other peak and every other trough of the second set of peaks and troughs is of increasing longitudinal extent in a proximal direction.

In some embodiments, as shown by way of example in FIG. 4, every other peak and every other trough of the first set of peaks and troughs is of increasing longitudinal extent in a distal direction and every other peak and every other trough of the second set of peaks and troughs is of increasing longitudinal extent in a proximal direction. Thus, peaks 106*a,c,e,g* are of increasing longitudinal extent in a distal direction. Peaks 106*b,d,f,h* are of also increasing longitudinal extent in a distal direction, although they are not of the same distal extent as peaks 106*a,c,e,g*. Peaks 106*g,i,k,m* are of decreasing longitudinal extent in a distal direction. Peaks 106*h,j,l* are of also decreasing longitudinal extent in a distal direction, although they are not of the same distal extent as peaks 106*h,j,l*. One or ordinary skill in the art will also recognize the same pattern in the troughs of the serpentine bands of FIG. 4.

Although connectors are not shown in FIG. 4, one of ordinary skill in the art will recognize that one or both of the serpentine bands shown in FIG. 4 may be used in a stent. The bands may be connected one to the other with one or more straight or curved connectors.

Figure 5:
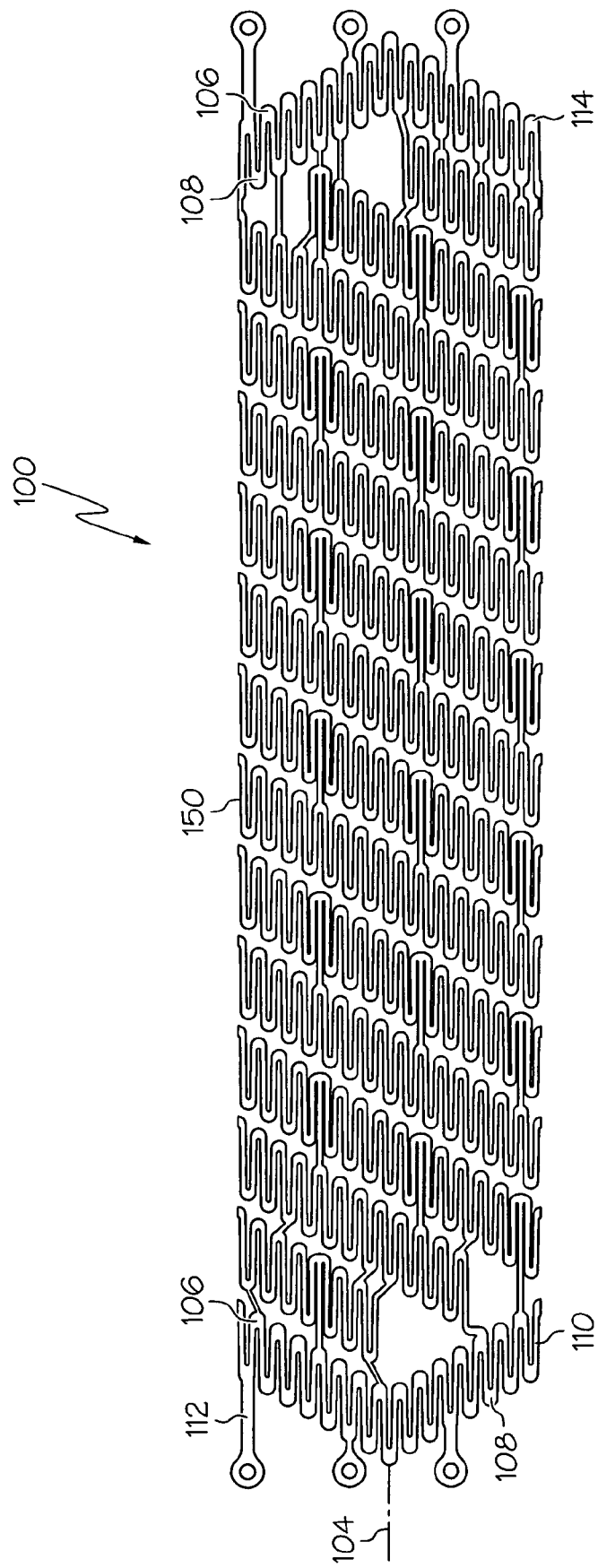
FIG. 5 shows an inventive helical stent.

In some embodiments of the invention, as shown by way of example in FIG. 5, the stent comprises two of the serpentine bands 110. One of the serpentine bands 110 is located at a proximal end 112 of the stent and the other of the serpentine bands is located at the distal end 114 of the stent. The stent includes a helical section 150 extending between the two serpentine bands. Helical section 150 includes a helical serpentine member having alternating peaks and troughs and struts extending therebetween. Other helical patterns may be used in the helical section of FIG. 5. The helical section may include one or more helical bands.

It is within the scope of the invention for the helical section that is employed in the inventive stents disclosed herein to be attached to the serpentine band at a single location or for the helical section to be attached to the serpentine band at a plurality of locations. It is within the scope of the invention for each end of the helical section to be attached at a single location to a serpentine band. It is also within the scope of the invention for each end of the helical section to be attached at a plurality of locations to a serpentine band. It is further within the scope of the invention for one end of the helical section to be attached at a plurality of locations to a serpentine band and the another end of the helical segment to be attached to a serpentine band at a single location.

In one or more embodiments, as shown in FIG. 5, the angle of at least a portion of the serpentine band at the end of the stent will match the angle of the helical section extending from the serpentine band at the end of the stent. As shown in FIG. 5, a portion of the end-most serpentine band is parallel to the helical section.

Figure 6:
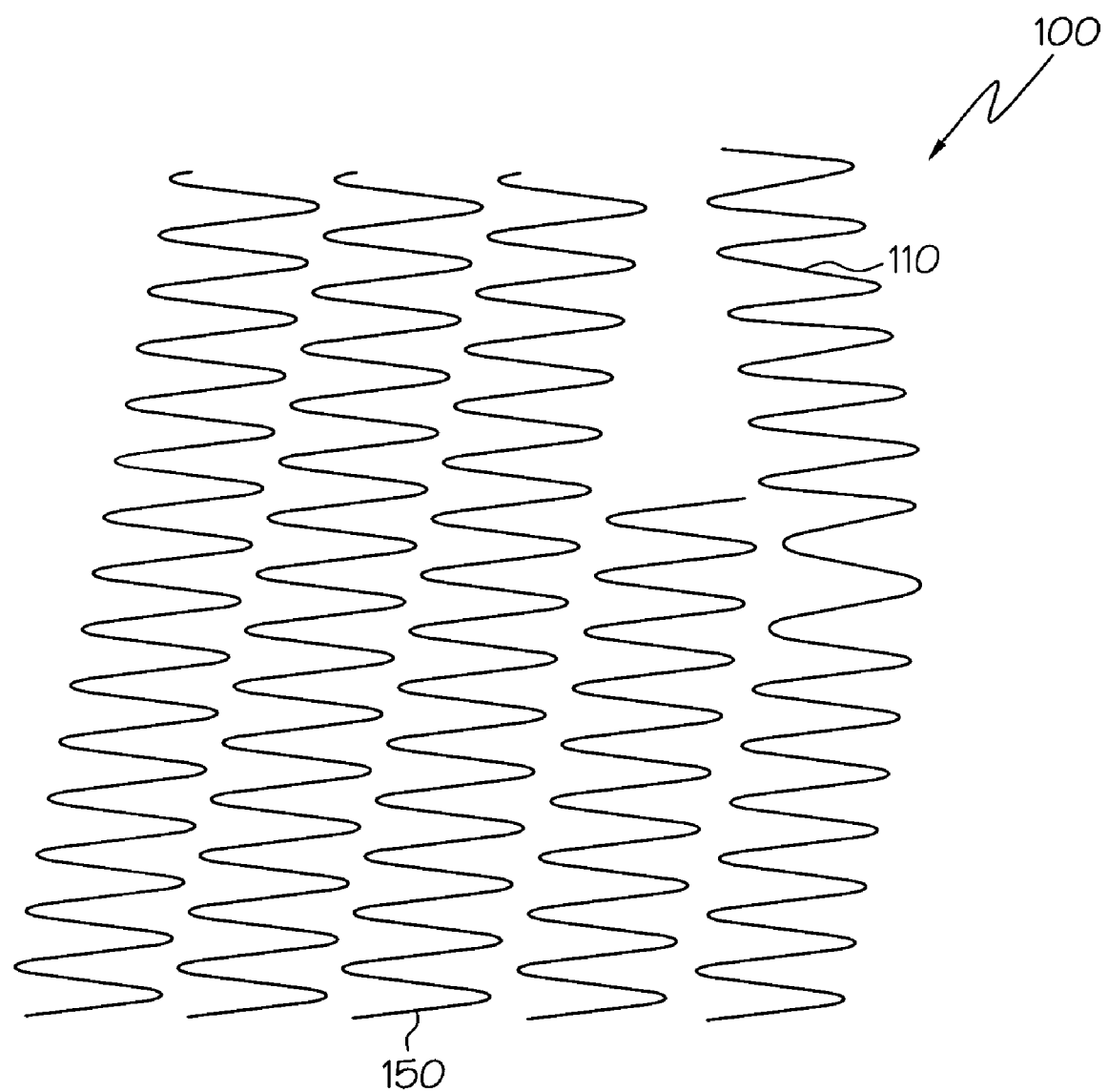
FIG. 6 shows another inventive helical stent.

Although the stent of FIG. 5 is shown with an inventive serpentine band at both ends of the stent, it is also within the scope of the invention for an inventive serpentine band to present at one end of the stent only. Optionally, a helical section could extend from the one inventive serpentine band. An example of such a stent is shown at 100 in FIG. 6.

It is further within the scope of the invention for one or more of the inventive serpentine bands to be combined with any other type of stent segment known in the art.

Figure 7B:
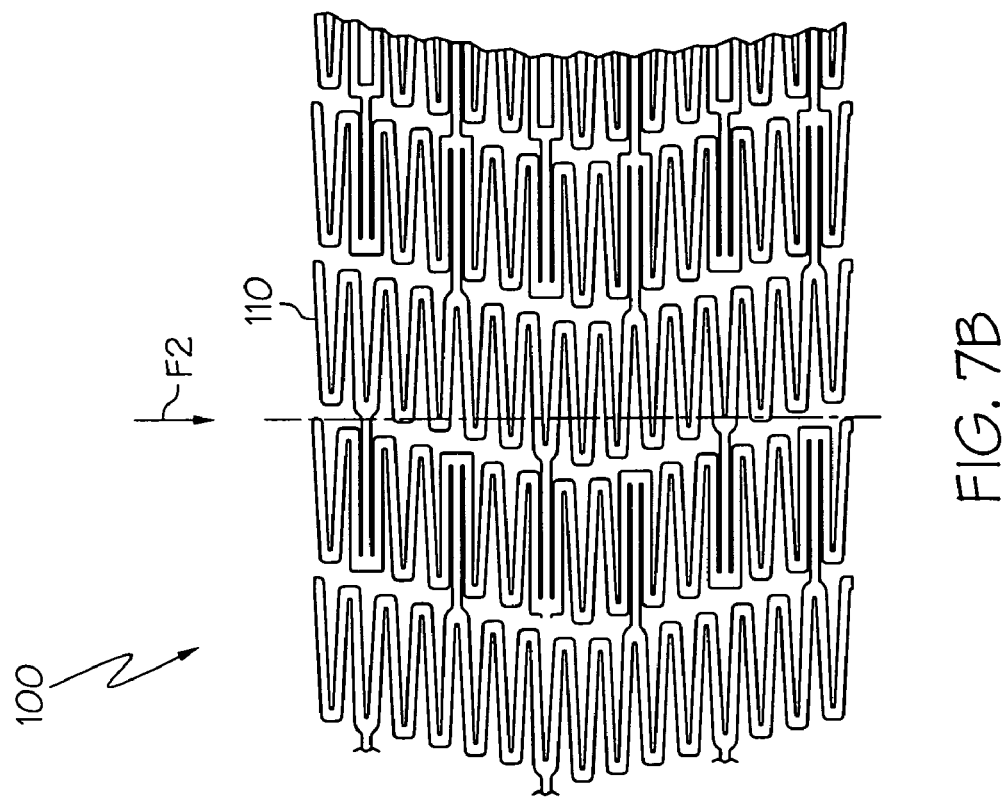
FIG. 7b shows a force being applied to a stent with inventive serpentine rings.
Figure 7A:
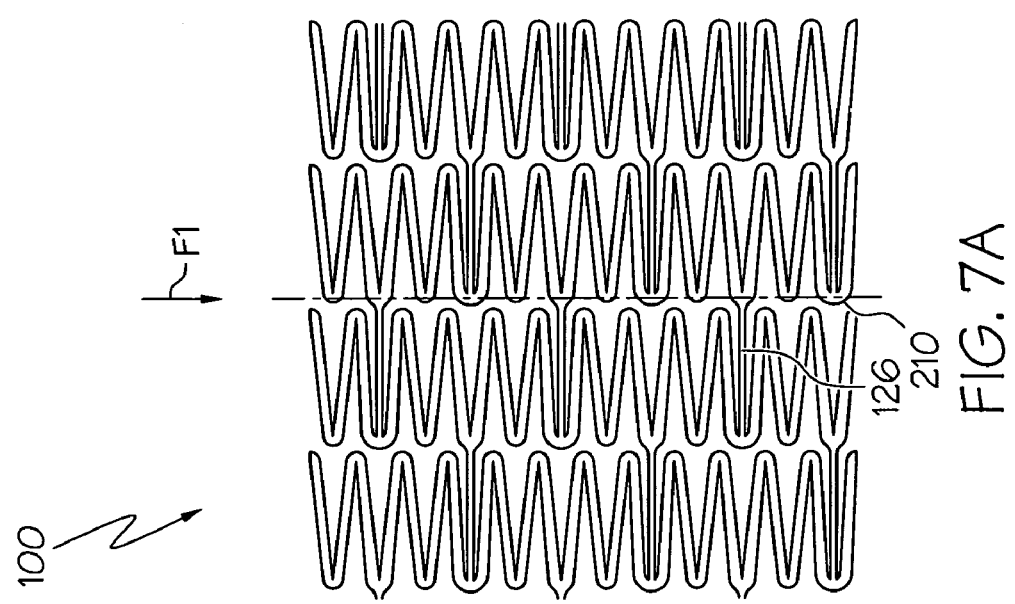
FIG. 7a shows a force being applied to a stent with standard serpentine rings.

Many of the inventive stents disclosed herein are better able to absorb radial forces than prior art stents having serpentine bands. FIGS. 7*a* and 7*b* depict forces being applied to a standard stent as well as to an embodiment of an inventive stent disclosed herein. As shown in FIG. 7*a*, the radial force directed in the area of the gap 210 between adjacent serpentine bands 110 is concentrated on the connectors 126 and the region where they connect with the serpentine bands. In the inventive stent of FIG. 7*b*, on the other hand, the radial force is spread along the struts in addition to a connector. This results in a better distribution of forces along the length of the stent which in turn results in better scaffolding.

The inventive stents, in many of the embodiments, may also be characterized as having pseudo-helical gaps between adjacent serpentine rings where the gaps are interrupted by connectors which connect adjacent helical bands. The gaps are pseudo-helical in that they have a shape which extends generally toward the distal end of the stent and then back toward the proximal end of the stent. The gap between any two adjacent bands may have two or more of such portions which extend distally and then turn back in a proximal direction.

The invention is also directed to a delivery system such as a catheter with an inventive stent disclosed herein disposed on the delivery system. The delivery catheter may be a balloon catheter or may be a catheter designed for delivery of self-expanding stents.

Typically, the stent will be reduced in size and disposed about a deliver catheter. The reduction in size typically entails reducing in size the diameter of the stent. The reducing in size and disposing of the stent about the catheter may occur simultaneously or in a plurality of steps. By way of non-limiting examples, the stent may be reduced in size and then disposed about a catheter followed by further reduction of the stent in size; the stent may also be disposed about the catheter and then reduced in size, in one or more reduction steps. In the case of balloon expandable stents, the stent may actual be crimped onto the balloon. In the case of self-expanding expanding stents, the stents may be crimped so that they fit within a retractable sheath.

Figure 8:
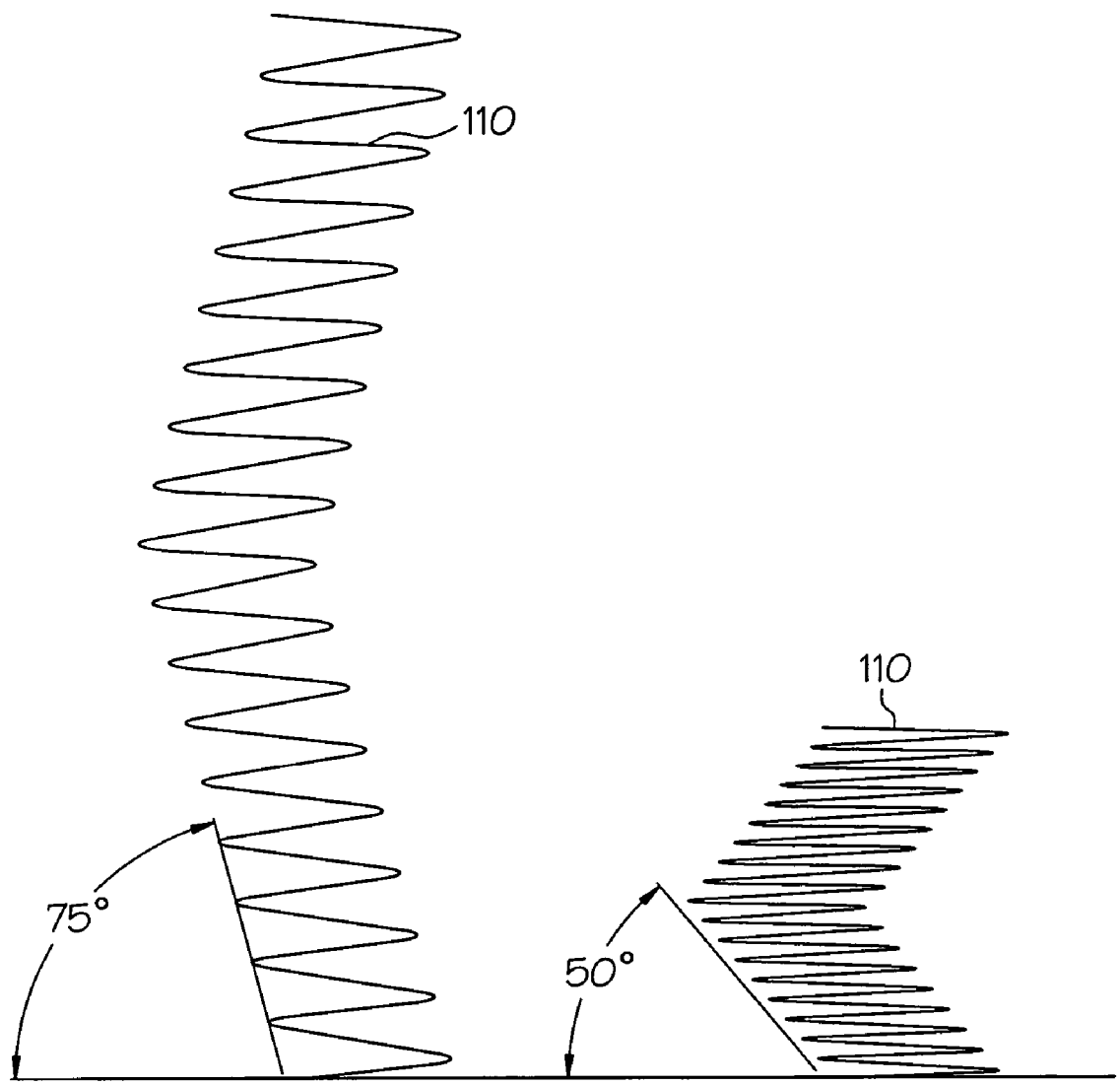
FIG. 8 shows a serpentine ring of an inventive stent in a crimped condition and in an uncrimped condition.

When the inventive stents disclosed herein are radially constrained by reducing in size or crimping, the angle that the serpentine bands makes with the respect to the longitudinal axis the stent will decrease and the slope increases. This is illustrated in FIG. 8. The angle between a portion of the band and the longitudinal axis decreases from 70 degrees to 50 degrees on crimping the stent. The other half of the band similarly has a decreased angle and increased slope.

In some embodiments of the invention, the angle of the angle will rage from 90 degrees to 45 degrees although other angles are within the scope of the invention as well.

Figure 9:
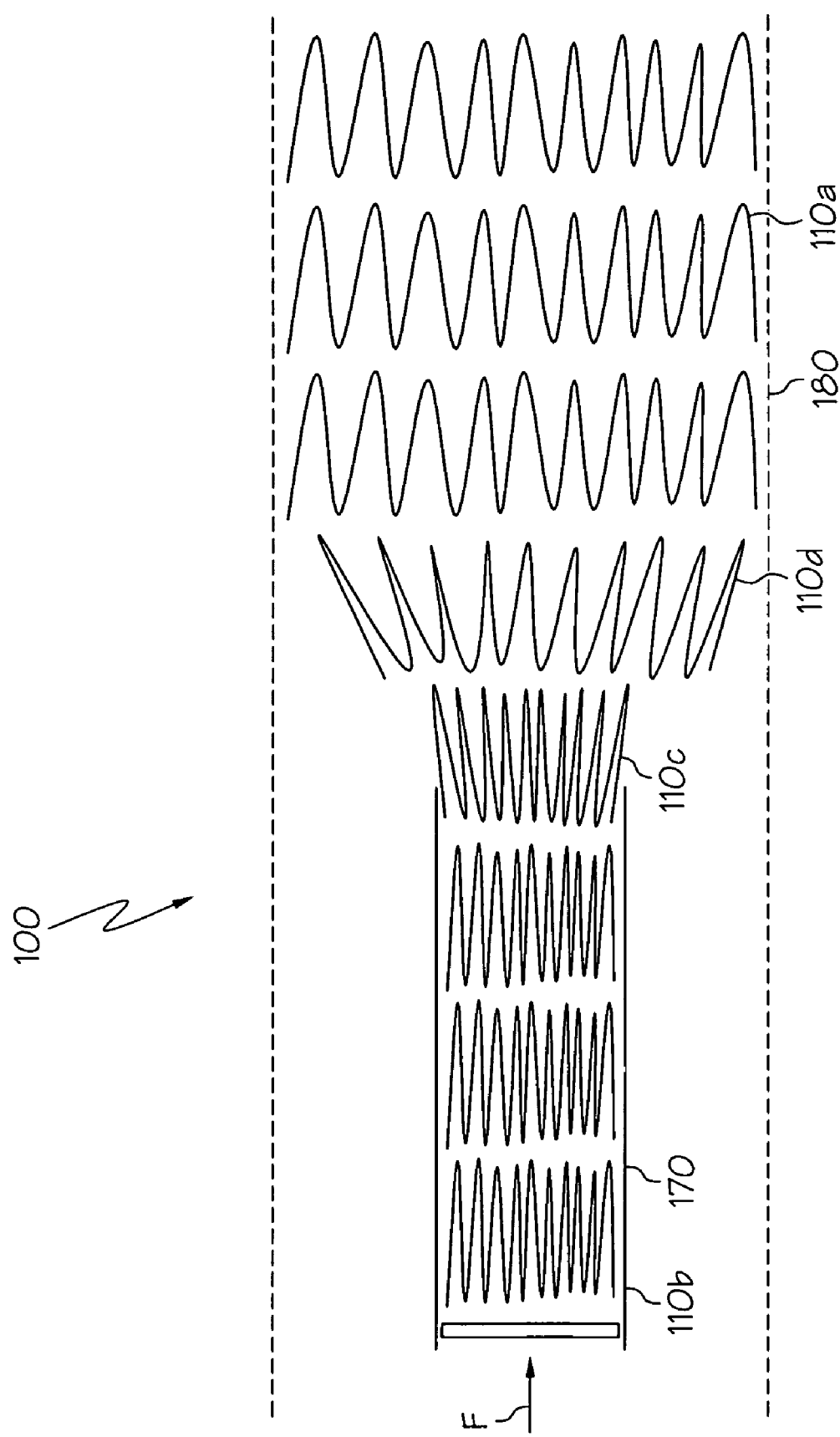
FIG. 9 shows a self-expanding stent with standard serpentine rings during expansion.

Typically, sheathed self-expanding stents formed of serpentine bands will experience jump forces as the sheath is withdrawn from the serpentine bands. This will occur because all of the serpentines within a band expand simultaneously where the struts are all of the same longitudinal extent. FIG. 9 illustrates such a stent at 100 in bodily lumen 180. Serpentine bands 110a and 110d are unsheathed. Serpentine band 110d is shown in the process of expanding. Serpentine band 110b is completely sheathed and serpentine band 110c is partially unsheathed.

Figure 10:
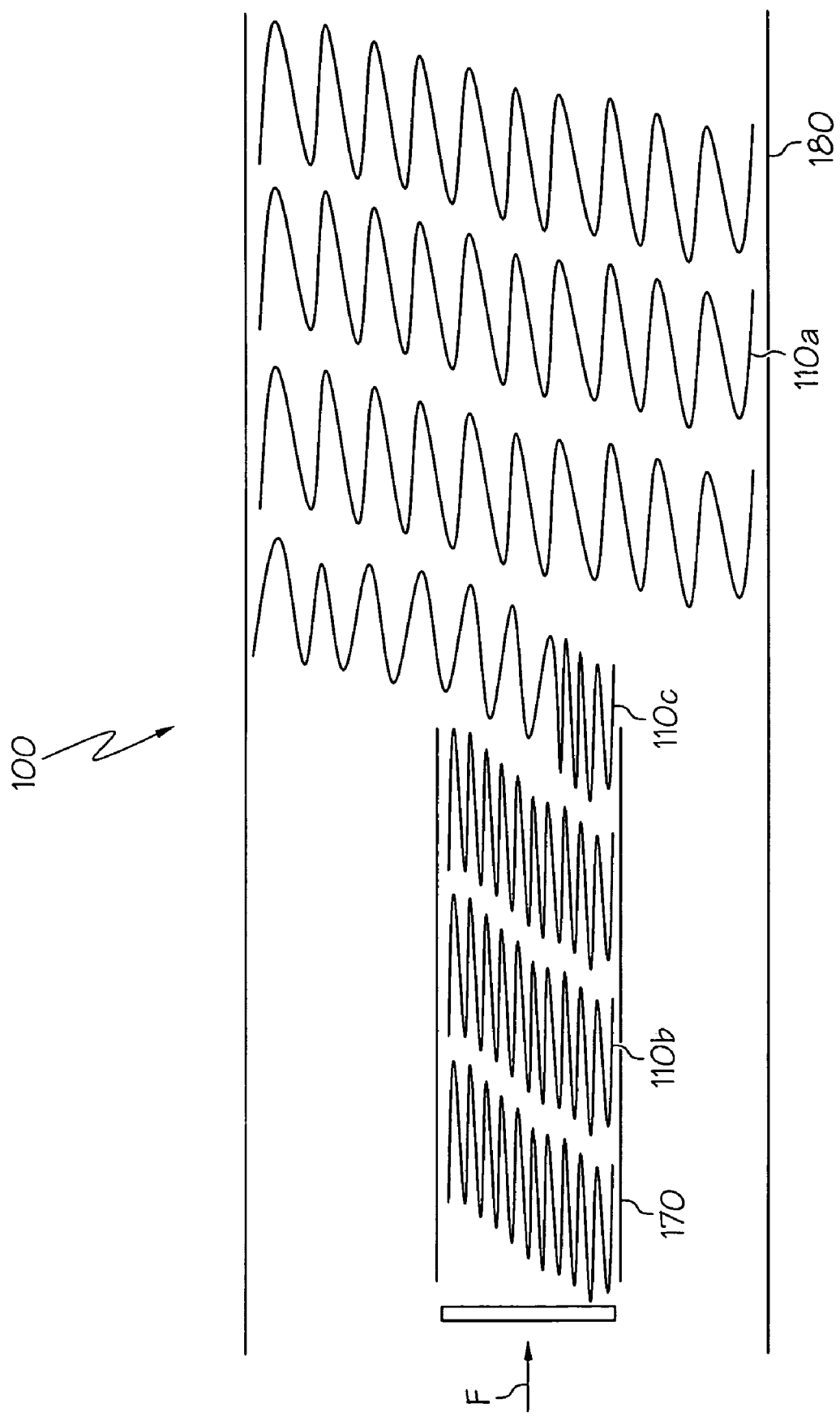
FIG. 10 shows an inventive stent during expansion.

The inventive stents, in self-expanding embodiments, do not experience the jump force to the same extent because as the sheath is withdrawn from a serpentine band, only some of the struts are initially unsheathed. This is shown in FIG. 10. Stent 100 is show partially released from sheath 170 within vessel 180. Serpentine band 110a is completely unsheathed, serpentine band 110b is completely sheathed and serpentine band 110c is partially unsheathed.

These and other embodiments which characterize the invention are pointed out with particularity in the claims annexed hereto and forming a part hereof. However, for additional understanding of the invention, its advantages and objectives obtained by its use, reference should be made to the drawings which form a further part hereof and the accompanying descriptive matter, in which there is illustrated and described embodiments of the invention.

The inventive stents may also be used in conjunction with graft material to provide a graft. The graft material may be disposed within the stent or outside the stent. The graft material may be coextensive with the stent or with only a portion of the stent. The graft material may extend all the way around the circumference of the stent or around only a portion of the stent.

The inventive stents disclosed herein may also be used as part of a stent having two or more branches. Examples of such stents include bifurcated stents.

The inventive stents disclosed herein may be tapered diameter or of uniform diameter in the expanded state. The taper may be uniform or non-uniform. The expanded stent may have two ends of a larger diameter than a middle section or only one end of larger diameter. The expanded stent may have a middle section of larger diameter than the ends of the stent. More generally, the expanded stent may have one or more portions of different diameter from other portions of the stent.

The inventive stents may have a constant wall thickness or a non-uniform wall thickness.

It is within the scope of the invention for the helical segment that is employed in the inventive stents disclosed herein to be attached to the ring section at a single location, as shown by way of example in FIG. 5b, or for the helical segment to be attached to the ring section at a plurality of locations, as shown by way of example in FIG. 5a. It is within the scope of the invention for each end of the helical segment to be attached at a single location to a ring segment. It is also within the scope of the invention for each end of the helical segment to be attached at a plurality of locations to a ring segment. It is further within the scope of the invention for one end of the helical segment to be attached at a plurality of locations to a ring segment and the another end of the helical segment to be attached to a ring segment at a single location.

The inventive stents may be made from any suitable biocompatible materials including one or more polymers, one or more metals or combinations of polymer(s) and metal(s). Examples of suitable materials include biodegradable materials that are also biocompatible. By biodegradable is meant that a material will undergo breakdown or decomposition into harmless compounds as part of a normal biological process. Suitable biodegradable materials include polylactic acid, polyglycolic acid (PGA), collagen or other connective proteins or natural materials, polycaprolactone, hylauric acid, adhesive proteins, co-polymers of these materials as well as composites and combinations thereof and combinations of other biodegradable polymers. Other polymers that may be used include polyester and polycarbonate copolymers. Examples of suitable metals include, but are not limited to, stainless steel, titanium, tantalum, platinum, tungsten, gold and alloys of any of the above-mentioned metals. Examples of suitable alloys include platinum-iridium alloys, cobalt-chromium alloys including Elgiloy and Phynox, MP35N alloy, nickel-titanium alloys, for example, Nitinol and nickel-titanium-platinum alloys.

The inventive stents may be made of shape memory materials such as superelastic Nitinol or spring steel, or may be made of materials which are plastically deformable. In the case of shape memory materials, the stent may be provided with a memorized shape and then deformed to a reduced diameter shape. The stent may restore itself to its memorized shape upon being heated to a transition temperature and having any restraints removed therefrom.

The inventive stents may be created by methods including cutting or etching a design from a tubular stock, from a flat sheet which is cut or etched and which is subsequently rolled or from one or more interwoven wires or braids. Any other suitable technique which is known in the art or which is subsequently developed may also be used to manufacture the inventive stents disclosed herein.

The stents disclosed herein may be used in any of the body lumens or vessels disclosed herein. At least some embodiments of the inventive stents may be of particular benefit when used in a superficial femoral artery (SFA) or in other regions where high axial and bending compliance is required.

The invention is also directed to methods of treatment of a bodily vessel using any of the inventive stents disclosed herein. In accordance with the method, a delivery system including a stent is inserted in a bodily vessel, including any of those disclosed herein. The stent is delivered to a desired bodily location and expanded via the use of a balloon, by withdrawing a restraining sheath or by any other suitable method. The delivery system is then removed from the body, with the stent remaining at the desired bodily location.

In some embodiments the stent, the delivery system or other portion of the assembly may include one or more areas, bands, coatings, members, etc. that is (are) detectable by imaging modalities such as X-Ray, MRI, ultrasound, etc. In some embodiments at least a portion of the stent and/or adjacent assembly is at least partially radiopaque.

In some embodiments the at least a portion of the stent is configured to include one or more mechanisms for the delivery of a therapeutic agent. Often the agent will be in the form of a coating or other layer (or layers) of material placed on a surface region of the stent, which is adapted to be released at the site of the stent's implantation or areas adjacent thereto.

A therapeutic agent may be a drug or other pharmaceutical product such as non-genetic agents, genetic agents, cellular material, etc. Some examples of suitable non-genetic therapeutic agents include but are not limited to: anti-thrombogenic agents such as heparin, heparin derivatives, vascular cell growth promoters, growth factor inhibitors, Paclitaxel, etc. Where an agent includes a genetic therapeutic agent, such a genetic agent may include but is not limited to: DNA, RNA and their respective derivatives and/or components; hedgehog proteins, etc. Where a therapeutic agent includes cellular material, the cellular material may include but is not limited to: cells of human origin and/or non-human origin as well as their respective components and/or derivatives thereof. Where the therapeutic agent includes a polymer agent, the polymer agent may be a polystyrene-polyisobutylene-polystyrene triblock copolymer (SIBS), polyethylene oxide, silicone rubber and/or any other suitable substrate.

The above disclosure is intended to be illustrative and not exhaustive. This description will suggest many variations and alternatives to one of ordinary skill in this art. The various elements shown in the individual figures and described above may be combined or modified for combination as desired. All these alternatives and variations are intended to be included within the scope of the claims where the term "comprising" means "including, but not limited to". Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of invention. Those skilled in the art may recognize other equivalents to the specific embodiment described herein which equivalents are intended to be encompassed by the claims attached hereto.

The invention claimed is:

1. A stent having a longitudinal axis, the stent having a proximal end and a distal end, the stent comprising a plurality of serpentine bands of increasing and decreasing extent, adjacent serpentine bands of increasing and decreasing extent connected one to another, each serpentine band of increasing and decreasing extent disposed about the longitudinal axis and having a plurality of proximal turns and distal turns interconnected by struts, the serpentine band of increasing and decreasing extent arranged in a pattern of increasing and decreasing extent in a proximal direction, the pattern including at least two sets of three or more consecutive interconnected proximal and distal turns of decreasing proximal extent followed by three or more consecutive interconnected proximal and distal turns of increasing proximal extent.

2. The stent of claim 1 wherein at least one of the plurality of serpentine bands of increasing and decreasing extent makes a plurality of complete windings around the longitudinal axis.

3. The stent of claim 1 where adjacent serpentine bands of increasing and decreasing extent are substantially in phase with one another.

4. A stent having a longitudinal axis, the stent having a proximal end and a distal end, the stent comprising a serpentine band at the proximal end of the stent, the serpentine band disposed about the longitudinal axis, the serpentine band having a plurality of proximal turns and distal turns interconnected by struts, the distal turns arranged in a pattern of increasing and decreasing extent in a proximal direction, the pattern including at least one set of three or more consecutive interconnected proximal and distal turns of decreasing proximal extent followed by at least one set of three or more consecutive interconnected proximal and distal turns of increasing proximal extent, the stent including a helical band extending from the serpentine band, the helical band forming a plurality of windings, each of the windings extending all the way around the longitudinal axis.

5. The stent of claim 4 comprising two of the serpentine bands, one of the serpentine bands located at a proximal end of the stent, the other of the serpentine bands at the distal end of the stent, the helical band connecting the two serpentine bands.

6. A stent comprising a serpentine band having a plurality of alternating peaks and troughs, a first portion of the serpentine band characterized by an envelope which is of generally increasing extent in a distal direction, every other peak in the first portion extending further in a distal direction than the peaks adjacent thereto, and a second portion of the serpentine band adjacent to the first portion and characterized by an envelope which is of generally decreasing extent in a distal direction, every other peak in the second portion being of decreased extent in a distal direction compared to the peaks adjacent thereto peaks and troughs.

7. The stent of claim 6 comprising a plurality of the serpentine band, adjacent serpentine bands connected one to the other.

8. The stent of claim 6 wherein the serpentine band forms a closed ring which extends about the longitudinal axis of the stent.

9. The stent of claim 6 wherein the serpentine band is at the proximal end of the stent, the stent including a helical portion extending from the serpentine band.

10. The stent of claim 6 comprising two of the serpentine bands, one of the serpentine bands located at a proximal end of the stent, the other of the serpentine bands at the distal end of the stent, the stent including a helical band extending between the two serpentine bands.

* * * * *